United States Patent [19]

Rentzea et al.

[11] Patent Number: 4,822,400
[45] Date of Patent: Apr. 18, 1989

[54] 1,3-DIOXAN-5-YLALKYLTRIAZOLES, THEIR USE FOR REGULATING PLANT GROWTH, AND AGENTS FOR THIS PURPOSE

[75] Inventors: Costin Rentzea, Heidelberg; Hubert Sauter, Mannheim; Wolfgang Tuerk, Ludwigshafen; Bernd Wenderoth, Lampertheim; Winfried Richarz, Stockstadt; Johann Jung; Wilhelm Rademacher, both of Limburgerhof, all of Fed. Rep. of Germany

[73] Assignee: BASF Aktiengesellschaft, Ludwigshafen, Fed. Rep. of Germany

[21] Appl. No.: 855,598

[22] Filed: Apr. 25, 1986

[30] Foreign Application Priority Data

Apr. 27, 1985 [DE] Fed. Rep. of Germany ....... 3515309

[51] Int. Cl.$^4$ .................. A01N 43/653; C07D 405/06
[52] U.S. Cl. ........................... 71/76; 71/92; 548/262; 549/372
[58] Field of Search ....................... 548/262; 71/76, 92

[56] References Cited

U.S. PATENT DOCUMENTS

| | | | |
|---|---|---|---|
| 4,319,911 | 3/1982 | Ammermann et al. | 71/76 |
| 4,328,028 | 5/1982 | Rentzea et al. | 71/76 |
| 4,380,546 | 4/1983 | Sauter et al. | 71/76 |
| 4,385,925 | 5/1983 | Rentzea et al. | 548/262 |
| 4,639,462 | 1/1987 | Kramer et al. | 548/262 |

FOREIGN PATENT DOCUMENTS 102543  8/1983  European Pat. Off. ............ 548/262

Primary Examiner—Richard L. Raymond
Assistant Examiner—Patricia L. Morris
Attorney, Agent, or Firm—Keil & Weinkauf

[57] ABSTRACT

Compounds of the formula I

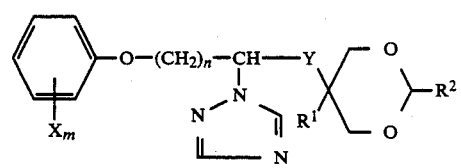

where $R^1$ and $R^2$ are identical or different and are each hyrogen or alkyl of 1 to 5 carbon atoms, the radicals X are identical or different substituents selected from the group consisting of halogen, cyano, trifluoromethyl, nitro, $C_1$-$C_4$-alkyl, $C_1$-$C_4$-alkoxy, unsubstituted or substituted phenyl or hydrogen, m is from zero to 5, n is an integer from 2 to 6 and Y is —CO— or —CH(OH)—, their intermediates of the formula (II)

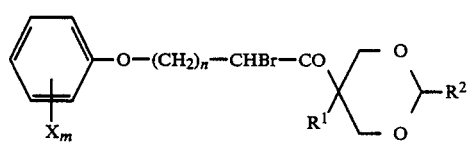

and (V)

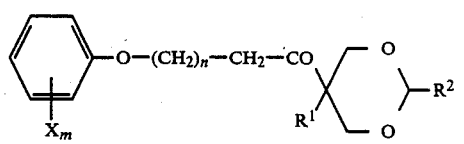

and the use of the compounds (I) as plant growth regulators.

5 Claims, No Drawings

1,3-DIOXAN-5-YLALKYLTRIAZOLES, THEIR USE FOR REGULATING PLANT GROWTH, AND AGENTS FOR THIS PURPOSE

The present invention relates to novel 1,3-dioxan-5-ylalkyltriazoles, processes for their preparation and plant growth regulators containing these compounds.

It is known that certain 2-haloethyl-trialkylammonium halides possess plant growth-regulating properties (cf. U.S. Pat. No. 3,156,554). Thus, plant growth can be influenced using (2-chloroethyl)-trimethylammonium chloride. However, the effectiveness of this substance is not always satisfactory, especially at low application rates.

It is also known that 3,3-dimethyl-2-(1,2,4-triazol-1-1-yl)-1-(4-chlorobenzoyl)-butane can be used for regulating plant growth (German Laid-Open Application DOS No. 2,739,352).

Furthermore, the plant growth-regulating action of 3,3-dimethyl-2-(1,2,4-triazol-1-(4-chlorobenzoyl)-butane (German Laid-Open Application DOS No. 2,921,168) and of 1-(5-methyl-1,3-dioxan-5-yl)-2-(1,2,4-triazol-1-yl)-3-(4-trifuoromethylphenyl-propen-1-ol (German Laid-Open Application DOS No. 3,026,140) is known.

At least in the case of specific target orgnanisms, the action of the compounds which are known growth regulators is unsatisfactory in respect of application rate, lack of side effects and morphospecific effect.

We have found that compounds of the formula I

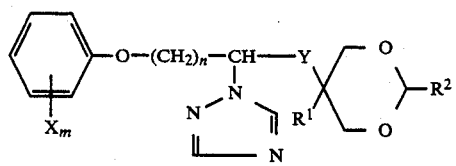

where $R^1$ and $R^2$ are identical or different and are each hydrogen or alkyl of 1 to 5 carbon atoms, the radicals X are identical or different substituents selected from the group consisting of halogen, cyano, trifluoromethyl, nitro, $C_1$-$C_4$-alkyl, $C_1$-$C_4$-alkoxy, unsubstituted or substituted phenyl and hydrogen, m is from zero to 5, n is an integer from 2 to 6 and Y is —CO— or —CH(OH)—, are very useful for influencing plant growth and are very well tolerated by plants; in the latter case the compounds are diastereomers comprising in each case two pairs of antipodes (enantiomers), which can have the configuration R*, S* or R*,R* at the two centers of chirality (cf. D. Seebach and V. Prelog, Angew. Chem. 94 (1982), 696 and the literature stated therein.

The present invention relates to both the diastereomers or diasteromeric mixtures and to the pure enantiomers obtainable in a conventional manner.

$R^1$ and $R^2$ are each preferably hydrogen, methyl, ethyl, n-propyl, isopropyl, n-butyl, sec-butyl, isobutyl, tert-butyl, n-pentyl or neopentyl.

$X_m$ is preferably hydrogen, 2-fluoro-, 4-fluoro-, 2-chloro-, 3-chloro-, 4-chloro-, 4-bromo-, 2,4-dichloro-, 2,6-dichloro-, 3,4-dichloro, 2,4,6-trichloro-, 2-chloro-4-methyl, 2-methyl-4-chloro-, 2-methyl-, 3-methyl-, 4-methyl-, 4-ethyl-, 4-isopropyl-, 4-tert-butyl-, 2,4-dimethyl-, 2,4,6-trimethyl-, 2-methoxy-4-methyl-, 2-methoxy-, 4-methoxy-, 4-ethoxy-, 2-trifluoromethyl-, 4-trifluoromethyl-, 4-cyano-, 4-nitro- or 4-phenyl-.

The novel compounds can be prepared by a process in which (a) 1,2,4-triazole is reacted with an appropriate α-bromoketone of the formula II

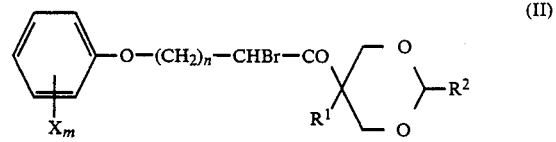

or (b) an appropreated aryloxyalkyl halide of the formula III

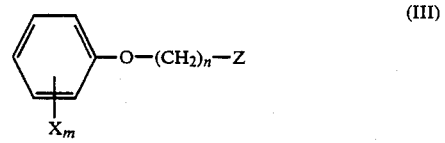

where Z is halogen (chlorine or bromine), is reacted with an appropriate 1-(1,3-dioxan-5-yl)-2-(1,2,4-triazolyl)ethan-1-one of the formula IV

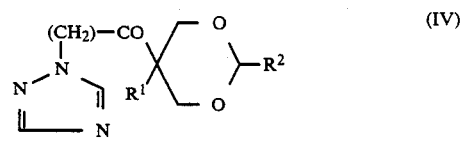

and, if required, the resulting compound is then reduced from the ketone to the secondary alcohol.

Reactions (a) and (b) can be carried out similarly in a conventional manner, as can the reduction of ketone to the alcohol. Some of the reactants in these reactions are known (cf. European Pat. No. 69,290 and German Laid-Open Application DOS No. 3,025,879).

The bromoketones of the formula II arenovel compounds and can be obtained, for example, by bromination of appropriate compounds of the formula V

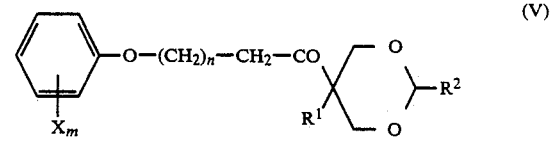

with bromine in formamide (H. Bredereck et al., Chem. Ber. 93 (1960), 2083) or with dioxane dibromide (S. J. Pasariber and L. R. Williams, Aust. J. Chem. 26 (1973), 1327) or with the COmplex (pyrrolidone)$_3$.HBr.Br$_2$ (D. C. Awang et al., Can. J. Chem. 47 (1969) 706).

The 1-(1,3-dioxan-5-yl)-2-(1,2,4-triazol-1-yl)-ethan-1-ones of the formula IV can be obtained, for example, by reacting an appropriate 2-holo-1-(2,5-dialkyl-1,3-dioxan-5-yl)-ethan-1-one of the formula VI

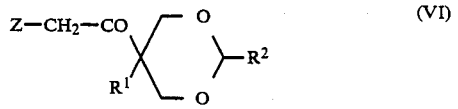

with 1,2,4-triazole or its alkali metal salt in a suitable solvent.

The haloketones of the formula VI are obtained, for example, by brominating a known 1,3-dioxan-5-ylethan-1-one of the formula VII

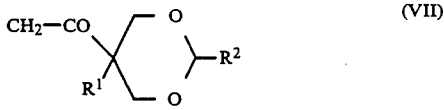

(VII)

where $R^1$ and $R^2$ have the above meanings, for example with a pyrrolidone-bromine complex, according to D. P. Wyman and P. R. Kaufmann, J. Org. Chem. 29 (1964), 1956.

The ketones obtained as described in (a) or (b) can, if desired, be reduced stereoselectively, this being done in a conventional manner (a) with a secondary alcoholate (EP-A-11 191), (b) with an alkylmagnesium halide which contains an alkyl radical of 2 to 6 carbon atoms and a beta hydrogen atom in the alkyl radical (cf. O.Z. 0050/36557) or (c) with hydrogen in the presence of ruthenium or a ruthenium derivative, in particular ruthenium oxide hydroxide (cf. O.Z. 0050/36557).

The resulting alcohols of te formula I have a substantially higher content of the diastereomers with the R*,S* configuration than those with the R*,R* configuration. The content of the R*,R* diastereomers in the mixture is as a rule well below 30%. Pure R*,S* diastereomers can be obtained from this mixture simply by washing the crude products with suitable solvents, eg. diisopropyl ether, or by recrystallization or another, conventional purification step, eg. chromatography.

In the diastereoselective reduction of the ketones with a complex hydride, preferably sodium borohydride, a metod which is likewise known per se, the resulting alcohols have a substantially higher content of the diastereomers with the R*,R* configuration.

EXAMPLE 1

(a) Preparation of an intermediate (aa) A solution of 498 g (1 mole) of pyrrolidone-bromine complex in 1 l of tetrahydrofuran is added dropwise to a solution of 144 g (1 mole) of 5-acetyl-5-methyl-1,3-dioxene and 85.5 g (1 mole) of pyrrolidone in 500 ml of tetrahydrofuran in the course of 2 hours at 50° C. Stirring is continued for 8 hours at 50° C., after which the white precipitate of pyrrolidone hydrobromide is filtered off under suction and washed with 50 ml of tetrahydrofuran, and the filtrate is evaporated down under reduced pressure. 220 g (99%) of crude, oily 1-(5-methyl-1,3-dioxan-5-yl)-2-brommoethan-1-one are obtained.

(ab) A solution of 223 g (1 mole) of 1-(5-methyl-1,3-dioxan-5-yl)-2-bromoethan-1-one in 200 ml of tetrahydrofuran is added dropwise, at 25° C. in the course of 2 hours, to a stirred suspension of 110.1 g (1.1 moles) of sodium 1,2,4-triazolide in 300 ml of dry tetrahydrofuran, the suspension being kept under nitrogen. The mixture is refluxed for 8 hours, after which the inorganic precipitate is filtered off and the filtrate is evaporated down to half its volume.

The mixture is seeded and left to stand overnight at +3° C. The precipitate is filtered off under suction, washed with 30 ml of cold (+5° C.) tetrahydrofuan, then with 80 ml of ether and then with 100 ml of n-pentane, and dried. 184 g (87.2%) of 1-(5-methyl-1,3-diox- an-;b 5-yl)-2-(1,2,4-triazol-1-yl)-ethan-1-one are obtained as white crystals of melting point 95°-97° C.

(b) Preparation of an end product (compound no. 1 in the Table)

A solution of 42.2 g (0.2 mole) of 1-(5-methyl-1,3-dioxan-5-yl)-2-(1,2,4-triazol-1-yl)-ethan-1-one in 150 ml of absolute dimethylformamide is added dropwise, at from 20° to 25° C., to a stirred suspension of 5.3 g (0.22 mole) of sodium hydride in 50 ml of absolute dimethylformamide, the suspension being kept under nitrogen. Stirring is continued for 3 hours, after which a solution of 49.4 g (0.2 mole) of 1-bromo-4-(2-fluorophenoxy)-butane in 50 ml of absolute dimethylformamide is added dropwise at 60° C. and the reaction mixture is then refluxed for a further 5 hours. About 100 ml of ice water are then carefully added dropwise at room temperature, and the mixture is extracted with three times 300 ml of methylene chloride. The organic phase is then washed several times with water, dried over Na$_2$SO$_4$ and evaporated down. Distillation (bp.=248° C./0.005) gives 56 g (74%) of 1-(5-methyl-1,3-dioxan-5-yl)-2-(1,2,4-triazol-1-yl)-6(2-fluorophenoxy)-hexan-1-one as a yellowish resin.

EXAMPLE 2

(1-R*,2-R*)-1-(5-Methyl-1,3-dioxan-5-yl)-2-(1,2,4-triazol-1-yl)-6-(2-fluorophenoxy)-hexan-1-ol (compound no. 2 in the Table)

3.0 g (0.078 mole) of sodium borohydride are added a little at a time to a solution of 24.5 g (0.065 mole) of 1-(5-methyl-1,3-dioxan-5-yl)-2-(1,2,4-triazol-1-yl)-6-(2-fluorophenoxy)-hexan-1-one in 300 ml of methanol at from 0° to +5° C. The stirred mixture is refluxed for 5 hours and then evaporated down, the residue is partitioned between 400 ml of ether and 200 ml of water, and the ether solution is washed three times with 200 ml of water, dried over sodium sulfate and again evaporated down. The residue is chromatographed over a silica gel column using a 9:1 methylene chloride/acetone mixture, and the solvent is removed. 13.2 g (54%) of the pure diastereomeric product are obtained in the form of white crystals of melting point 87°-89° C.

EXAMPLE 3

(1-R*,2-S*)-1-(5-Methyl-1,3-dioxan-5-yl)-2-(1,2,4-triazol-1-yl)-6-(2-fluorophenoxy)-hexan-1-ol (compound no. 3 in the Table)

A solution of 8.0 g (0.021 mole) of 1-(5-methyl-1,3-dioxan-5-yl)-6-(2-fluorophenoxy-hexan-1-one in 100 ml of dry tetrahydrofuran is added dropwise, under nitrogen, to a stirred solution of about 0.06 mole of n-propylmagnesium bromide, prepared in a conventional manner, in 100 ml of dry tetrahydrofuran, at the reflux temperature. When the solution is complete, the mixture is refluxed for a further 5 hours, after which it is hydrolyzed at 0° C. by the dropwise addition of 50 ml of water, and 50 ml of concentrated ammonium chloride solution are added. The mixture is extracted with three times 200 ml of diethyl ether, washed neutral with water, dried over magnesium sulfate and chromatographed over a silica gel column using a 9:1 metylene chloride/acetone mixture to give 3.5 g (44%) of the pure diastereomeric product as a pale yellow oil.

$^1$H-NMR (80 MHz/CDCl): =0.9 (S, 3H), 1.0-1.4 (m, 2H), 2.8 (m, 2H), 2.0-2.1 (m, 2H), 3.4 (2d, 2H), 3.8-4.2 (m, 6H), 4.6-4.7 (m, 2H), 4.95 (d, 1H), 6.8-7.1 (m, 4H), 7.95 (s, 1H), 8.15 (S, 1H).

A suitable characteristic feature of the R*,$* diastereomers is, for example, the fact that in the $^1$H-NMR spectrum the signal for the 3 protons of the methyl group on the dioxanyl radical occurs at 0.1–0.2 ppm, whereas the corresponding signal for the R*,S* diastereromer is at 0.8–1.0 ppm.

The compounds listed in the Table below were prepared by appropriately modifying the above data (Dia A=R*,R*-diastereomer; Dia-B=R*,S*-diastereomer).

TABLE 1

I

| Compound | $X_m$ | n | $R^1$ | $R^2$ | Y | Diastereomer | Mp. [°C.] | IR(Film)[cm$^{-1}$] |
|---|---|---|---|---|---|---|---|---|
| 1 | 2-F | 4 | $CH_3$ | H | —CO— | — | 91–93 | |
| 2 | 2-F | 4 | $CH_3$ | H | —CH(OH)— | A | 87–89 | |
| 3 | 2-F | 4 | $CH_3$ | H | —CH(OH)— | B | Oil | 3300, 2950, 2860, 1507, 1281, 1259, 1165, 1034, 926, 749 |
| 4 | 4-F | 4 | $CH_3$ | H | —CO— | — | Oil | |
| 5 | H | 4 | $CH_3$ | H | —CO— | — | 60–62 | |
| 6 | H | 4 | $CH_3$ | H | —CH(OH)— | A | Oil | 3310, 2860, 1479, 1247, 1162, 1027, 924, 755, 682 |
| 7 | H | 4 | $C_2H_5$ | H | —CO— | — | Oil | |
| 8 | H | 4 | $CH_3$ | $i$-$C_3H_7$ | —CO— | — | Oil | 2964, 1719, 1600, 1499, 1245, 1098, 756 |
| 9 | H | 4 | $CH_3$ | $i$-$C_3H_7$ | —CH(OH)— | A | Oil | 3300, 2962, 1601, 1499, 1474, 1245, 1098, 755 |
| 10 | H | 4 | $CH_3$ | $n$-$C_3H_7$ | CO— | — | Oil | |
| 11 | 2-Cl | 4 | $CH_3$ | H | —CO— | — | Oil | 2950, 2860, 1745, 1580, 1487, 1471, 1278, 1249, 1166, 1037, 927, 750 |
| 12 | 2-Cl | 4 | $CH_3$ | H | —CH(OH)— | A | Oil | 3240, 2940, 2860, 1487, 1278, 1164, 1063, 926 |
| 13 | 2-Cl | 4 | $CH_3$ | H | —CH(OH)— | B | Oil | 3310, 2950, 2870, 1487, 1279, 1251, 1166, 1062, 749 |
| 14 | 3-Cl | 4 | $CH_3$ | H | —CO— | — | Oil | |
| 15 | 3-Cl | 4 | $CH_3$ | H | —CH(OH)— | B | Oil | |
| 16 | 4-Cl | 4 | $CH_3$ | H | —CO— | — | resin | |
| 17 | 2,6-$Cl_2$ | 4 | $CH_3$ | H | —CO— | — | resin | |
| 18 | 2,4-$Cl_2$ | 4 | $CH_3$ | H | —CO— | — | Oil | 2950, 2860, 1745, 1485, 1470, 1289, 1267, 1258, 1166, 1162, 1066, 1034, 927 |
| 19 | 2,4-$Cl_2$ | 4 | $CH_3$ | H | —CH(OH)— | A | Oil | 3250, 2940, 1485, 1289, 1164, 1063, 926 |
| 20 | 2,4-$Cl_2$ | 4 | $CH_3$ | H | —CH(OH)— | B | resin | 3300, 2950, 1485, 1289, 1166, 1062, 1034 |
| 21 | 2-Cl, 4-$CH_3$ | 4 | $CH_3$ | H | —CO— | — | Oil | 2950, 2860, 1720, 1502, 1255, 1165, 1033, 927 |
| 22 | 2-Cl, 4-$CH_3$ | 4 | $CH_3$ | H | —CH(OH)— | A | Oil | 3240, 2940, 2860, 1502, 1254, 1164, 1030, 926 |
| 23 | 2-Cl, 4-$CH_3$ | 4 | $CH_3$ | H | —CH(OH)— | B | 105–106 | |

TABLE 1-continued

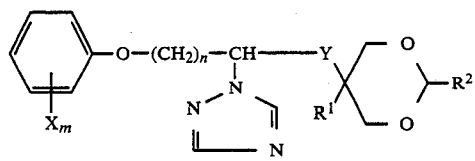

| Compound | $X_m$ | n | $R^1$ | $R^2$ | Y | Diastereomer | Mp. [°C.] | IR(Film)[cm$^{-1}$] |
|---|---|---|---|---|---|---|---|---|
| 24 | 2-CH$_3$, 4-Cl | 4 | CH$_3$ | H | —CO— | — | Oil | 2940, 2860, 1719, 1494, 1248, 1165, 1033, 927 |
| 25 | 2-CH$_3$, 4-Cl | 4 | CH$_3$ | H | OH<br>\|<br>—CH— | A | 73–76 | |
| 26 | 2-CH$_3$, 4-Cl | 4 | CH$_3$ | H | OH<br>\|<br>—CH— | B | Oil | 3350, 2941, 2860, 1494, 1248, 1165, 1033, 926 |
| 27 | 2-CH$_3$ | 4 | CH$_3$ | H | —CO— | — | resin | |
| 28 | 2-CH$_3$ | 4 | CH$_3$ | H | OH<br>\|<br>—CH— | A | Oil | |
| 29 | 2-CH$_3$ | 4 | CH$_3$ | H | OH<br>\|<br>—CH— | B | Oil | |
| 30 | 3-CH$_3$ | 4 | CH$_3$ | H | —CO— | — | resin | 2860, 1720, 1502, 1262, 1165, 1033, 927 |
| 31 | 3-CH$_3$ | 4 | CH$_3$ | H | OH<br>\|<br>—CH— | A | 100∝101 | |
| 32 | 3-CH$_3$ | 4 | CH$_3$ | H | OH<br>\|<br>—CH— | B | Oil | 3260, 2940, 2860, 1491, 1263, 1165, 1033, 926 |
| 33 | 4-CH$_3$ | 4 | CH$_3$ | H | —CO— | — | Oil | |
| 34 | 4-C$_2$H$_5$ | 4 | CH$_3$ | H | —CO— | — | resin | |
| 35 | 4-i-C$_3$H$_7$ | 4 | CH$_3$ | H | —CO— | — | Oil | 2958, 2868, 1745, 1512, 1243, 1166, 1034, 927, 829 |
| 36 | 4-i-C$_3$H$_7$ | 4 | CH$_3$ | H | OH<br>\|<br>—CH— | A | 74–77 | |
| 37 | 4-i-C$_3$H$_7$ | 4 | CH$_3$ | H | OH<br>\|<br>—CH— | B | Oil | 3300, 2958, 2868, 1512, 1243, 1166, 1034, 927, 829 |
| 38 | 2-OCH$_3$ | 4 | CH$_3$ | H | —CO— | — | Oil | 2950, 2865, 1740, 1505, 1254, 1227, 1166, 1124, 1031, 927, 746 |
| 39 | 2-OCH$_3$ | 4 | CH$_3$ | H | OH<br>\|<br>—CH— | A | 117–119 | |
| 40 | 2-OCH$_3$ | 4 | CH$_3$ | H | OH<br>\|<br>—CH— | B | Oil | 3260, 2940, 1506, 1253, 1165, 1030, 745 |
| 41 | 4-OCH$_3$ | 4 | CH$_3$ | H | —CO— | — | resin | |
| 42 | 4-OC$_2$H$_5$ | 4 | CH$_3$ | H | —CO— | — | resin | |
| 43 | 4-NO$_2$ | 4 | CH$_3$ | H | —CO— | — | Oil | 2938, 2862, 1745, 1600, 1499, 1245, 1187, 1084, 1034, 927, 757 |
| 45 | H | 5 | CH$_3$ | H | OH<br>\|<br>—CH— | A | Oil | 3120, 2940, 1499, 1245, 1163, 1027, 926, 753 |
| 46 | H | 5 | CH$_3$ | H | OH<br>\|<br>—CH— | B | 88–90 | |
| 47 | 2-F | 5 | CH$_3$ | H | —CO— | — | Oil | 2940, 1725, 1507, 1457, 1279, 1259, 1166, 1035, 937, 750 |

TABLE 1-continued

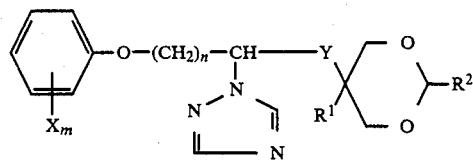

| Compound | $X_m$ | n | $R^1$ | $R^2$ | Y | Diastereomer | Mp. [°C.] | IR(Film)[cm$^{-1}$] |
|---|---|---|---|---|---|---|---|---|
| 48 | 2-F | 5 | CH$_3$ | H | OH\|—CH— | A | Oil | 3250, 2940, 1507, 1259, 1164, 1034, 750 |
| 49 | 2-F | 5 | CH$_3$ | H | OH\|—CH— | B | 78–80 | |
| 50 | H | 3 | CH$_3$ | i-C$_3$H$_7$ | —CO— | — | Oil | 2963, 1719, 1600, 1499, 1245, 1098, 755 |
| 51 | H | 3 | CH$_3$ | i-C$_3$H$_7$ | OH\|—CH— | A | 110–114 | |
| 52 | H | 3 | CH$_3$ | H | —CO— | — | Oil | 2860, 1720, 1599, 1500, 1245, 1166, 1033, 927, 757 |
| 53 | H | 3 | CH$_3$ | H | OH\|—CH— | A | 68–70 | |
| 54 | H | 3 | CH$_3$ | H | OH\|—CH— | B | 95–100 | |
| 55 | 3-F | 3 | CH$_3$ | H | —CO— | — | Oil | |
| 56 | 2-F | 3 | CH$_3$ | H | —CO— | — | Oil | 2860, 1720, 1506, 1259, 1165, 1034, 927, 751 |
| 57 | 2-F | 3 | CH$_3$ | H | OH\|—CH— | A | Oil | 3250, 2860, 1507, 1259, 1164, 1032, 926, 750 |
| 58 | 2-F | 3 | CH$_3$ | H | OH\|—CH— | B | 125–127 | |
| 59 | 2,4-Cl$_2$ | 3 | CH$_3$ | H | —CO— | — | resin | |
| 60 | 3-CH$_3$ | 3 | CH$_3$ | H | —CO— | — | Oil | 2860, 1720, 1502, 1262, 1165, 1033, 927 |
| 61 | 3-CH$_3$ | 3 | CH$_3$ | H | OH\|—CH— | A | 100–103 | |
| 62 | 3-CH$_3$ | 3 | CH$_3$ | H | OH\|—CH— | B | 103–106 | |
| 63 | 4-CH$_3$ | 3 | CH$_3$ | H | —CO— | — | Oil | 2860, 1720, 1512, 1243, 1106, 1033, 927 |
| 64 | 4-CH$_3$ | 3 | CH$_3$ | H | OH\|—CH— | A | 102–104 | 3230, 2859, 1512, 1243, 1164, 1031, 926 |
| 65 | 4-CH$_3$ | 3 | CH$_3$ | H | OH\|—CH— | B | 105–107 | |
| 66 | 4-C$_6$H$_5$ | 3 | CH$_3$ | H | —CO— | — | resin | |
| 67 | 4-NO$_2$ | 3 | CH$_3$ | H | —CO— | — | resin | |
| 68 | 4-OC$_2$H$_5$ | 3 | CH$_3$ | H | —CO— | — | resin | |
| 69 | 2-Cl, 4-CH$_3$ | 3 | CH$_3$ | H | —CO— | — | Oil | 2860, 1721, 1502, 1255, 1166, 1033, 927 |
| 70 | 2-Cl, 4-CH$_3$ | 3 | CH$_3$ | H | OH\|—CH— | A | 100–103 | |
| 71 | 2-Cl, 4-CH$_3$ | 3 | CH$_3$ | H | OH\|—CH— | B | 152–154 | |

TABLE 1-continued

Structure I:

Phenyl ring with $X_m$ substituents, connected via $-O-(CH_2)_n-CH(-)-Y-C(R^1)(CH_2O-)(CH_2O-)CH-R^2$ (1,3-dioxane), and with an N-N=CH-N (1,2,4-triazol-1-yl) group on the CH.

| Compound | $X_m$ | n | $R^1$ | $R^2$ | Y | Diastereomer | Mp. [°C.] | IR(Film)[cm$^{-1}$] |
|---|---|---|---|---|---|---|---|---|
| 72 | 2-CH$_3$, 4-Cl | 3 | CH$_3$ | H | —CO— | — | Oil | 2860, 1721, 1495, 1248, 1191, 1165 |
| 73 | 2-CH$_3$, 4-Cl | 3 | CH$_3$ | H | OH\|—CH— | A | 135–138 | |
| 74 | 2-CH$_3$, 4-Cl | 3 | CH$_3$ | H | OH\|—CH— | B | Oil | 3200, 2860, 1494, 1248, 1165, 1033, 926 |
| 75 | 2-CH$_3$, 4-CH$_3$ | 4 | CH$_3$ | H | —CO— | — | Oil | 2940, 2866, 1719, 1503, 1254, 1165, 1034, 927 |
| 76 | 2-CH$_3$, 4-CH$_3$ | 4 | CH$_3$ | H | OH\|—CH— | A | 68–70 | |
| 77 | 2-CH$_3$, 4-CH$_3$ | 4 | CH$_3$ | H | OH\|—CH— | B | Oil | 3270, 2941, 2861, 1505, 1254, 1165, 1033, 926 |
| 78 | 2-CH$_3$, 4-CH$_3$ | 3 | CH$_3$ | H | —CO— | — | Oil | 2860, 1721, 1504, 1258, 1228, 1166, 1033, 927 |
| 79 | 2-CH$_3$, 4-CH$_3$ | 3 | CH$_3$ | H | OH\|—CH— | A | 75–78 | |
| 80 | 2-CH$_3$, 4-CH$_3$ | 3 | CH$_3$ | H | OH\|—CH— | B | 116–118 | |
| 81 | H | 2 | CH$_3$ | H | —CO— | — | resin | |
| 82 | H | 2 | CH$_3$ | H | OH\|—CH— | A | resin | 3240, 2840, 1580, 1480, 1240, 1150, 1040, 920, 750 |
| 83 | H | 2 | CH$_3$ | H | OH\|—CH— | B | resin | |
| 84 | H | 2 | CH$_3$ | i-C$_3$H$_5$ | —CO— | — | Oil | 2960, 1718, 1600, 1500, 1244, 1098, 1005, 756 |
| 85 | H | 2 | CH$_3$ | i-C$_3$H$_5$ | OH\|—CH— | A | 119–124 | |
| 86 | 2-F | 2 | CH$_3$ | H | —CO— | — | Oil | 2860, 1740, 1507, 1166, 1034, 927, 752 |
| 87 | 2-F | 2 | CH$_3$ | H | OH\|—CH— | A | 69–72 | 3250, 2855, 1507, 1260, 1164, 1033, 926, 750 |
| 88 | 2-F | 2 | CH$_3$ | H | OH\|—CH— | B | Oil | 3300, 2850, 1507, 1260, 1165, 1034, 926, 750 |
| 89 | 4-F | 2 | CH$_3$ | H | —CO— | — | Oil | |
| 90 | 2-Cl | 2 | CH$_3$ | H | —CO— | — | Oil | |
| 91 | 4-Cl | 2 | CH$_3$ | H | —CO— | — | Oil | 2840, 1700, 1480, 1230, 1160, 1020, 920, 820 |
| 92 | 4-Cl | 2 | CH$_3$ | H | OH\|—CH— | A | 121–123 | |
| 93 | 4-Br | 2 | CH$_3$ | H | —CO— | — | Oil | |
| 94 | 4-Br | 2 | CH$_3$ | H | OH\|—CH— | A | 129–131 | |
| 95 | 4-CN | 2 | CH$_3$ | i-C$_3$H$_5$ | —CO— | — | Oil | 2960, 2226, 1740, 1607, |

TABLE 1-continued

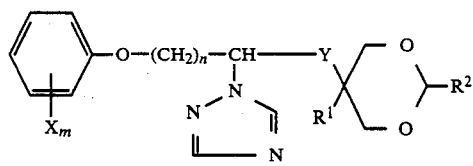

| Compound | $X_m$ | n | $R^1$ | $R^2$ | Y | Diastereomer | Mp. [°C.] | IR(Film)[cm$^{-1}$] |
|---|---|---|---|---|---|---|---|---|
| 96 | 4-CN | 2 | $CH_3$ | i-$C_3H_7$ | -CH(OH)- | A | 110-118 | 1509, 1258, 1174, 1097, 1005 |
| 97 | 2-$CF_3$ | 2 | $CH_3$ | H | -CO- | — | Oil | 2860, 1750, 1609, 1500, 1461, 1323, 1278, 1166, 1119, 1037 |
| 98 | 2-$CF_3$ | 2 | $CH_3$ | H | -CH(OH)- | A | 99-104 | |
| 99 | 2-$CF_3$ | 2 | $CH_3$ | H | -CH(OH)- | B | 112-117 | |
| 100 | 4-$CF_3$ | 2 | $CH_3$ | H | -CO- | — | Oil | |
| 101 | 4-$CF_3$ | 2 | $CH_3$ | H | -CH(OH)- | A | Oil | |
| 102 | 2-$CH_3$ | 2 | $CH_3$ | H | -CO- | — | Oil | 2860, 1722, 1497, 1245, 1165, 1123, 1032, 927, 755 |
| 103 | 2-$CH_3$ | 2 | $CH_3$ | H | -CH(OH)- | A | 74-77 | 3260, 2850, 1497, 1245, 1164, 1086, 1032, 926 |
| 104 | 2-$CH_3$ | 2 | $CH_3$ | H | -CH(OH)- | B | 131-133 | |
| 105 | 3-$CH_3$ | 2 | $CH_3$ | H | -CO- | — | Oil | 2860, 1721, 1491, 1262, 1165, 1033, 927 |
| 106 | 3-$CH_3$ | 2 | $CH_3$ | H | -CH(OH)- | A | 79-81 | |
| 107 | 3-$CH_3$ | 2 | $CH_3$ | H | -CH(OH)- | B | 97-98 | |
| 108 | 2,4-$Cl_2$ | 2 | $CH_3$ | H | -CO- | — | 108-110 | |
| 109 | 2,4-$Cl_2$ | 2 | $CH_3$ | H | -CH(OH)- | A | 122-124 | |
| 110 | 2,4,6-$Cl_3$ | 2 | $C_2H_5$ | H | -CO- | — | resin | |
| 111 | 2-Cl, 4-$CH_3$ | 2 | $CH_3$ | H | -CO- | — | Oil | 2860, 1723, 1502, 1166, 1033, 927 |
| 112 | 2-Cl, 4-$CH_3$ | 2 | $CH_3$ | H | -CH(OH)- | A | 101-103 | |
| 113 | 2-Cl, 4-$CH_3$ | 2 | $CH_3$ | H | -CH(H)- | B | Oil | 3260, 2860, 1502, 1166, 1033, 926 |
| 114 | 2-$CH_3$, 4-Cl | 2 | $CH_3$ | H | -CO- | — | 88-90 | |
| 115 | 2-$CH_3$, 4-Cl | 2 | $CH_3$ | H | -CH(OH)- | A | 102-105 | |
| 116 | 2-$CH_3$, 4-Cl | 2 | $CH_3$ | H | -CH(OH)- | B | 121-123 | |
| 117 | 2-$CH_3$, 4-$CH_3$ | 2 | $CH_3$ | H | -CO- | — | Oil | 2860, 1721, 1505, 1255, 1165, 1033, 925 |

TABLE 1-continued

I

| Compound | $X_m$ | n | $R^1$ | $R^2$ | Y | Diastereomer | Mp. [°C.] | IR(Film)[cm$^{-1}$] |
|---|---|---|---|---|---|---|---|---|
| 118 | 2-CH$_3$, 4-CH$_3$ | 2 | CH$_3$ | H | OH<br>$\mid$<br>—CH— | A | 73–76 | |
| 119 | 2-CH$_3$, 4-CH$_3$ | 2 | CH$_3$ | H | OH<br>$\mid$<br>—CH— | B | 75–78 | |
| 120 | 2-OCH$_3$, 4-CH$_3$ | 2 | CH$_3$ | H | —CO— | — | resin | 2860, 1720, 1512, 1266, 1164, 1140, 1034, 927 |
| 121 | 2-OCH$_3$, 4-CH$_3$ | 2 | CH$_3$ | H | OH<br>$\mid$<br>—CH— | B | resin | |
| 122 | 2-OCH$_3$, 4-CH$_3$ | 2 | CH$_3$ | H | OH<br>$\mid$<br>—CH— | B | resin | 3280, 2960, 1512, 1164, 1033, 926 |

To determine the growth-regulating property of the test substances, test plants were grown on a culture substrate provided with sufficient nutrients, in plastic containers about 12.5 cm in diameter.

The substances to be tested were sprayed as an aqueous formulation onto the plants by the post-emergence method. The growth-regulating effect observed was supported at the end of the experiment by measuring the growth in height. Measured values obtained in this manner were expressed as a ratio of the growth in height of the untreated plants. The comparative substances used were chlorocholine chloride and the active ingredients denoted below by B, C and D.

Parallel with the reduction in the growth in height, the color intensity of the leaves increased. Because of the increased chlorophyll content, a higher rate of photosynthesis and hence a greater yield are also expected.

Comparatives substances:

A Chloroquinoline chloride of the formula

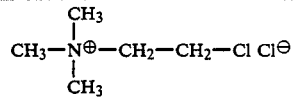

B

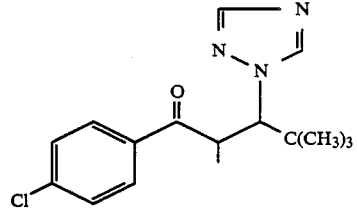

C

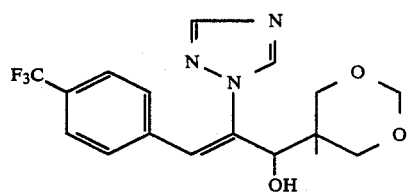

D

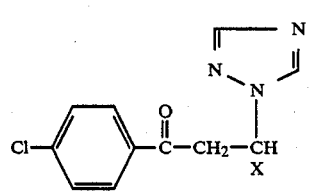

In experiments with spring barley, sunflowers and summer rape, and in the rice seedling test, it was found that, at application rates of 1.5 and 6 mg of active ingredient per container, the compounds 3, 5, 8, 9, 50, 51, 82, 84, 85, 92, 95, 96, 108, 109, 114 and 115 all had a more advantageous and reduction in the height of growth.

We claim:

1. A compound of the formula I

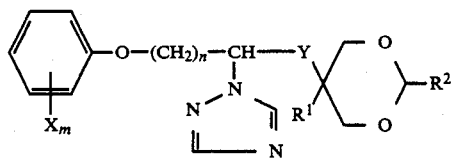 (I)

where $R^1$ and $R^2$ are identical or different and are each hydrogen or alkyl of 1 to 5 carbon atoms, X is an identical or different substituent selected from the group consisting of halogen, cyano, trifluoromethyl, nitro, $C_1$-$C_4$-alkyl, $C_1$-$C_4$-alkoxy, unsubstituted phenyl or hydrogen, m is from zero to 5, n is an integer from 2 to 6 and Y is —CO— or —CH(OH)—.

2. A compound of the formula I as defined in claim 1, wherein X is hydrogen, 2-fluoro-, 4-fluoro-, 2-chloro-, 3-chloro-, 4-chloro-, 4-bromo-, 2,4-dichloro-, 2,6-dichloro-, 3,4-dicholoro-, 2,4,6-trichloro-, 2-chloro-4-methyl-, 2-methyl-4-chloro-, 2-methyl-, 3-methyl-, 4-methyl-, 4-ethyl-, 4-isopropyl-, 4-tert-butyl-, 2,4-dimethyl-, 2,4,6-trimethyl-, 2-methoxy-4-methyl-, 2-methoxy-, 4-methoxy-, 4-ethoxy-, 2-trifluoromethyl-, 4-trifluoromethyl-, 4-cyano-, 4-nitro- or 4-phenyl-, $R^1$ is methyl or ethyl and $R^2$ is hydrogen, methyl, ethyl, n-propyl, isopropyl, n-butyl, sec-butyl, isobutyl, tert-butyl, n-pentyl or neopentyl.

3. A method of reducing the height of growing plants which comprises: applying to the plants or their habitat an effective amount of one or more compounds of the formula I as defined in claim 1.

4. A method of reducing the height of growing plants which comprises: applying to the plants or their habitat an effective amount of one or more compounds of the formula I as defined in claim 2.

5. A composition for reducing the height of growing plants which comprises: an effective amount of one or more compounds of the formula I as defined in claim 1, and an inert liquid or solid carrier.

* * * * *